US012697074B2

(12) United States Patent　　　　　(10) Patent No.: US 12,697,074 B2

Neumann　　　　　　　　　　　　　　(45) Date of Patent:　　Aug. 4, 2026

(54) SYSTEMS AND METHODS OF GENERATING A FOOD COMPATIBILITY DATUM

(71) Applicant: KPN Innovations, LLC, Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 345 days.

(21) Appl. No.: 18/591,331

(22) Filed: Feb. 29, 2024

(65) Prior Publication Data

US 2024/0197263 A1　　Jun. 20, 2024

Related U.S. Application Data

(63) Continuation-in-part of application No. 17/517,801, filed on Nov. 3, 2021, now Pat. No. 11,931,186, (Continued)

(51) Int. Cl.
　　A61B 5/00　　　　(2006.01)
　　A61B 90/00　　　(2016.01)
　　　　(Continued)

(52) U.S. Cl.
　　CPC .............. A61B 5/7267 (2013.01); A61B 5/48 (2013.01); A61B 5/7246 (2013.01); (Continued)

(58) Field of Classification Search
　　CPC ... A61B 5/14532; A61B 5/14546; A61B 5/48; A61B 5/4836; A61B 5/7246; A61B 5/7267; A61B 5/7435; A61B 90/39; G06N 20/00; G16H 20/60; G16H 40/63; G16H 50/20; G16H 50/70

See application file for complete search history.

(56)　　　　　References Cited

U.S. PATENT DOCUMENTS 6,692,916 B2　　2/2004　Bevilacqua et al.
7,761,309 B2　　7/2010　Sacco et al.
　　　　(Continued)

OTHER PUBLICATIONS https://diginole.lib.fsu.edu/islandora/object/fsu%3A507684/datastream/PDF/view.

*Primary Examiner* — Scott Luan

(74) *Attorney, Agent, or Firm* — Caldwell LLC

(57)　　　　　ABSTRACT

Described herein are systems and methods of generating a food compatibility datum. In some embodiments, a system may include a computing device configured to receive a plurality of physiological extractions of a subject, wherein the plurality of physiological extractions comprises at least an inflammation metric; receive a plurality of alimentary element consumption data wherein each alimentary element consumption datum of the plurality of plurality of alimentary element consumption data describes a consumption of the subject prior to a physiological extraction of the plurality of physiological extractions; generate a plurality of alimentary element compatibility data; identify an inflammatory alimentary element as a function of the plurality of alimentary element compatibility data; pair a medical professional with the subject as a function of the inflammatory alimentary element; and display the inflammatory alimentary element using a user interface at a display device.

20 Claims, 11 Drawing Sheets

Related U.S. Application Data which is a continuation of application No. 17/007,251, filed on Aug. 31, 2020, now Pat. No. 11,179,110.

(51) Int. Cl.

| | | |
|---|---|---|
| *G06N 20/00* | (2019.01) | |
| *G16H 20/60* | (2018.01) | |
| *G16H 40/63* | (2018.01) | |

(52) U.S. Cl.
CPC ............ *A61B 5/7435* (2013.01); *A61B 90/39* (2016.02); *G06N 20/00* (2019.01); *G16H 20/60* (2018.01); *G16H 40/63* (2018.01)

(56) References Cited

U.S. PATENT DOCUMENTS

| | | |
|---|---|---|
| 7,853,626 B2 | 12/2010 | Jung et al. |
| 7,953,613 B2 | 5/2011 | Gizewski |
| 8,388,530 B2 | 3/2013 | Shusterman |
| 9,492,114 B2 | 11/2016 | Reiman |
| 10,085,643 B2 | 10/2018 | Bandic et al. |
| 2018/0284141 A1 | 10/2018 | Ayton et al. |
| 2019/0027249 A1 | 1/2019 | Fuksenko et al. |

905 Receiving Physiological Extraction of a User

910 Generating an Inflammation Metric of a User

915 Identifying at Least an Alimentary Element for Reducing Inflammation

920 Providing, to a User, the Alimentary Element

900

SYSTEMS AND METHODS OF GENERATING A FOOD COMPATIBILITY DATUM

CROSS-REFERENCE TO RELATED APPLICATIONS

This application is a continuation-in-part of Non-provisional application Ser. No. 17/517,801, filed on Nov. 3, 2021, and entitled "METHOD OF SYSTEM FOR REVERSING INFLAMMATION IN A USER," which is a continuation of Non-provisional application Ser. No. 17/007,251, filed on Aug. 31, 2020, now U.S. Pat. No. 11,179,110, and entitled "METHOD OF SYSTEM FOR REVERSING INFLAMMATION IN A USER" the entirety of each of which is incorporated herein by reference.

FIELD OF THE INVENTION

The present invention generally relates to the field of machine-learning. In particular, the present invention is directed to methods and systems for reversing inflammation in a user.

BACKGROUND

Worldwide, 3 in 5 people perish due to chronic inflammatory diseases like stroke, respiratory disease, heart disorder, cancers, obesity, and diabetes. Efficient method for identifying and developing strategies to identify and reverse inflammation in users is hindered by diversity in individual cohorts. Moreover, lifestyle preferences and difficulty in changing those preferences complicate adherence to strategies for reducing and reversing inflammation.

SUMMARY OF THE DISCLOSURE

In an aspect, a system for generating a food compatibility datum, may include a computing device configured to receive a plurality of physiological extractions of a subject, wherein the plurality of physiological extractions includes at least an inflammation metric; receive a plurality of alimentary element consumption data wherein each alimentary element consumption datum of the plurality of plurality of alimentary element consumption data describes a consumption of the subject prior to a physiological extraction of the plurality of physiological extractions; generate a plurality of alimentary element compatibility data, wherein each alimentary element compatibility datum of the plurality of alimentary element compatibility data is associated with at least an alimentary element consumption datum of the plurality of alimentary element consumption data, wherein generating the plurality of alimentary element compatibility data includes training an alimentary element compatibility machine learning model on a training dataset including a plurality of example physiological extractions and a plurality of example alimentary element consumption data as inputs correlated to a plurality of example alimentary element compatibility data as outputs; and generating an alimentary element compatibility datum as a function of the at least an inflammation metric and the plurality of alimentary element consumption data using the trained alimentary element compatibility machine learning model; identify an inflammatory alimentary element as a function of the plurality of alimentary element compatibility data; pair a medical professional with the subject as a function of the inflammatory alimentary element; and display the inflammatory alimentary element using a user interface at a display device.

In another aspect, a method of generating a food compatibility datum may include, using at least a processor, receiving a plurality of physiological extractions of a subject, wherein the plurality of physiological extractions includes at least an inflammation metric; using the at least a processor, receiving a plurality of alimentary element consumption data wherein each alimentary element consumption datum of the plurality of plurality of alimentary element consumption data describes a consumption of the subject prior to a physiological extraction of the plurality of physiological extractions; using the at least a processor, generating a plurality of alimentary element compatibility data, wherein each alimentary element compatibility datum of the plurality of alimentary element compatibility data is associated with at least an alimentary element consumption datum of the plurality of alimentary element consumption data, wherein generating the plurality of alimentary element compatibility data includes training an alimentary element compatibility machine learning model on a training dataset including a plurality of example physiological extractions and a plurality of example alimentary element consumption data as inputs correlated to a plurality of example alimentary element compatibility data as outputs; and generating an alimentary element compatibility datum as a function of the at least an inflammation metric and the plurality of alimentary element consumption data using the trained alimentary element compatibility machine learning model; using the at least a processor, identifying an inflammatory alimentary element as a function of the plurality of alimentary element compatibility data; using the at least a processor, pairing a medical professional with the subject as a function of the inflammatory alimentary element; and using the at least a processor, displaying the inflammatory alimentary element using a user interface at a display device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for reversing inflammation in a user. In an embodiment, system includes a computing device designed and configured to receive physiological extraction of a user, wherein physiological extraction contains at least an inflammation marker. Computing device may use a machine-learning model to generate inflammation metrics of a user, wherein the model can differentiate between types of inflammation markers and assign quantitative metrics to the user for their overall inflammation. System may identify, according to the inflammation metric, at least an alimentary element for reversing inflammation and potentially reverse inflammation in the user. In an embodiment, system may provide, to the user, an alimentary element for reversing inflammation, and accept inputs from the user regarding alimentary elements, and suggest alimentary elements based on the effect it would have on the inflammation metric, providing a recipe for potentially using the alimentary elements. Alternatively or additionally, exemplary embodiments may accept inflammation metrics for a plurality of users and suggest an alimentary element and recipe for using that alimentary element, wherein the recipe would improve inflammation metrics in the plurality of users.

Figure 1:
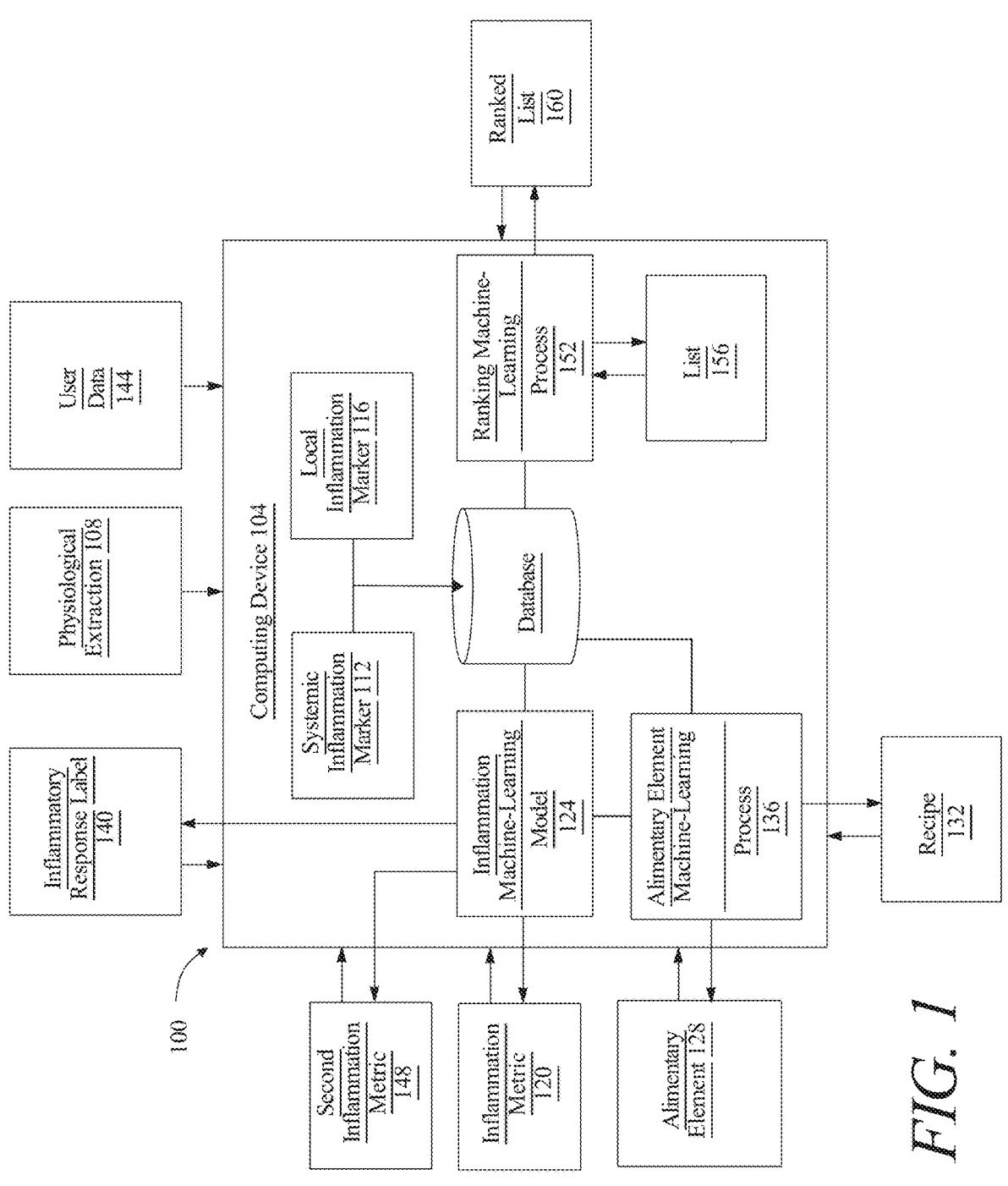
FIG. 1 is a block diagram illustrating an exemplary embodiment of a system of reversing inflammation in a user.

Referring now to FIG. 1, an exemplary embodiment of a system 100 for reversing inflammation in a user is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 is further designed and configured to receive physiological extraction of a user. "Physiological extraction" as used in this disclosure is any element of biological extraction data, wherein biological extraction data refers to any biomarker, genetic data or epigenetic indication, microbiome, or any chemical, biological, or physiological markers of data of a user, including for instance, and without limitation, as described in U.S. Nonprovisional application Ser. No. 16/885,647, filed on Jul. 22, 2020, and entitled "METHODS AND SYSTEMS FOR DETERMINING A PLURALITY OF DIMENSIONS OF BIOLOGICAL EXTRACTION USER DATA AND ARTIFICIAL INTELLIGENCE," the entirety of which is incorporated herein by reference.

Still referring to FIG. 1, physiological extraction 108 may refer to blood chemistry, for instance blood protein and enzyme concentrations and activities for instance of fibrinogen, ferritin, serum amyloid A, $\alpha$-1-acid glycoprotein, ceruloplasmin, hepcidin, haptoglobin, tumor necrosis factor-$\alpha$ (TNF-α), among other acute phase proteins; for instance cytokine identities and concentrations for instance inter-leukin-6 (IL-6); blood metabolites identifies and concentra-tions such as blood sugar, LDL and HDL cholesterol con-tent; hormones identities and concentrations such as insulin, androgens, cortisol, thyroid hormones, and the like; eryth-rocyte sedimentation rate, blood cell counts, plasma viscos-ity, and other biochemical, biophysical, and physiological properties regarding blood panels, blood tests, and the like, as it relates to biomarkers of inflammation.

Continuing to refer to FIG. 1, physiological extraction 108 may refer to data concerning genetics of a user and epigenetic analysis, for instance as derived from a physical biological sample derived from hair, skin, saliva, and the like. Epigenetic analysis of inflammation may include enu-meration of DNA methylation, acetylation, and other post-translational modifications, presence and concentration of regulatory factors, small non-coding RNAs, and the like.

Continuing to refer to FIG. 1, physiological extraction 108 may include medical history information including, for instance and without limitation, diagnoses, medications, conditions, mental and physical evaluations, and the like. Medical history information may include gut wall strength evaluations among other physical health data, may include a history of surgeries that may be important to inflammation, for instance reconstructions, plastic surgeries, use of pros-thetics, and the like. Medical history information may include current and past medications, including over-the-counter remedies and medications, for instance and without limitation non-steroidal anti-inflammatory drugs (NSAIDs).

Still referring to FIG. 1, physiological extraction 108 may include microbiome data that describes, for instance, iden-tities, amounts, chemical signatures, metabolites, signaling peptides, and the like, of bacteria, fungi, protists, parasites, viruses, and other microbiological entities and organisms that may provide information about a user's inflammation.

Continuing to refer to FIG. 1, physiological extraction 108 may include data regarding exposure to environmental factors including chemicals, inhalational irritants, pollen, exposure to allergens, fibers, spores, and the like. Environ-mental factors present in physiological extraction that may contribute to inflammation may include housing integrity factors such as the presence of leaded products, asbestos, mold, and the like.

Continuing to refer to FIG. 1, physiological extraction 108 may include user lifestyle data such as sleep patterns, duration, and schedules, diet and food selections, supple-ments, exercise frequency, duration, activities, and the like. Persons skilled in the art, upon review of this disclosure in its entirety, will be aware of the types of data of a user that may be used as physiological extraction for purposes described herein.

Still referring to FIG. 1, in some embodiments, system 100 may continuously receive physiological extractions of a subject. For example, subject may wear a device which continuously takes measurements and transmits them to system 100. System 100 may identify a subset of continu-ously received physiological extractions as a function of alimentary element consumption timing. Alimentary ele-ment consumption data is described below. A subset of physiological extractions may be relevant to determining inflammatory effects of alimentary elements based on rela-tive timing of consumption of alimentary elements and measurement of physiological extraction. For example, a physiological extraction most relevant for determining inflammatory effects of a consumed alimentary element may be one measured within a certain time frame while the alimentary element has significant effects on inflammation of a subject.

Continuing to refer to FIG. 1, physiological extraction 108 of a user contains at least an inflammation marker. An "inflammation marker," as used in this disclosure is a physiological element indicative of diagnosing and/or moni-toring inflammatory conditions. Inflammatory markers may be indicative of and/or associated with inflammatory con-ditions, for instance and without limitation, infections, auto-immune conditions, cancers, physical exertion, sleep depri-vation, among many other conditions. At least an inflammation marker may include a systemic inflammation marker. As used in this disclosure "systemic inflammation marker" is a marker indicative of a background level of chronic inflammation present in a user. For instance and without limitation, systemic inflammation marker 112 may relate to C-reactive protein (CRP) concentration and oligo-meric state identified from a user blood sample, erythrocyte sedimentation rate (ESR), procalcitonin (PCT) concentra-tion, and the like, that may not be related to any particular disease, injury, trauma, among other diagnosable conditions. In further non-limiting illustrative examples, systemic inflammation markers may be hormonal profiles, liver func-tion tests for aspartate transaminase (AST), alanine transaminase (ALT), total protein level and albumin content, and the like that may signify chronic inflammation from exercise, tissue damage, longstanding injury, repetitive motion, and the like. Systemic inflammation marker 112 may relate to a general level of inflammation in a user that may subsist despite no known underlying tissue damage, injury and/or trauma. A user with a clinical manifestation that is otherwise normal may have measurable background markers of inflammation that are a part of normal physiol-ogy. These markers, such as those described above, may be systemic inflammation markers 112 of a user's basal, back-ground level of inflammation.

Continuing in reference to FIG. 1, at least an inflamma-tion marker may include a local inflammation marker. As used in this disclosure "local inflammation marker" is a marker indicating a localized level of acute inflammation present in a user. For instance and without limitation, local inflammation marker 112 may refer to biomarkers associated with acute injury, infection, trauma, and diseases, such as a soft-tissue injury, temporary condition, curable or address-able condition. In non-limiting illustrative examples, local-ized aggressive periodontitis (LAP) is a condition in users that can be measured by assessing a physical gingival crevicular fluid (GCF) sample and evaluating for the pres-ence of and concentrations of proteins, enzymes, cytokines, and other signaling molecules. In such an example, common local inflammatory markers 116 may be (TNF-α), IL-1β, IL-2, IL-4, IL-6, IL-8, IL-10, IL12p40, granulocyte-macro-phage colony-stimulating factor (GMCSF), monocyte che-moattractant protein-1 (MCP-1), among other factors. More-over, in users affected by LAP, microbiome data regarding endotoxin concentration from bacteria present in the mouth, nose, throat, sinus, and the like, may be 4-5+ times higher than those who do not suffer from LAP, wherein proportions of endotoxin protein concentration may be a local inflam-mation marker 116 caused by bacterial infections.

Continuing in reference to FIG. 1, computing device 104 may generate an inflammation metric of a user, wherein generating the inflammation metric may include using an inflammation machine-learning model, the inflammation machine-learning model may be trained using training data that enumerates hallmarks of inflammation in a user with quantitative measurements of inflammation. An "inflammation metric," as used in this disclosure, is a quantitative value that describes systemic inflammation, local inflammation, or both of a subject. An inflammation metric may include an identified source of inflammation. In some embodiments, an inflammation metric may include a measurement of a level of an inflammation marker, such as a local inflammation marker or a systemic inflammation marker or both. In some embodiments, an inflammation metric may include a value calculated from measurements of levels of a plurality of inflammation markers, as described further herein. An inflammation metric 120 may be expressed as a numerical value, function, vector, matrix, or any other suitable form of organizing quantitative data relating to a user's systemic and local inflammation as determined by their physiological extraction 108 data. An inflammation machine-learning model may be any suitable machine-learning algorithm or process that may be performed by a machine-learning module, as described in further detail below.

Inflammation machine-learning model 124 may train with training data that corresponds to, for instance and without limitation, healthy and/or normal physiological levels of inflammation markers, wherein the normal range is associated with a numerical score, for instance as a percentile score, and a user's inflammation marker level corresponds to a numerical value relative the range of scores in the model. In such an example, the inflammation machine-learning model 124 may perform this function for each inflammation marker identified in the user physiological extraction 108 data. In non-limiting exemplary embodiments, a user may have hundreds of pieces of inflammation data present in their physiological extraction that may relate to known healthy ranges of inflammation markers that can be related to some quantitative scale. In non-limiting illustrative examples, the inflammation machine-learning model 124 may locate and train with data that indicates a normal range of IL-6 may be 0-16.4 picograms/milliliter (pg/mL) with a mean of 6.0 pg/mL wherein the mean is set of a nominal score of '0' and the lower limit of 0 pg/mL, indicating no inflammatory marker present in a healthy individual showing no IL-6 indication of inflammation may be set of a score of +10, with negative scores for IL-6 concentrations above the mean. In such an example, having maximal scores for other inflammation markers may be impacted by negative values of <−10 for inflammation marker concentrations that exceed upper ranges found in healthy, normal, and even non-healthy, abnormal individuals. In this manner of scoring, having a concerningly high level of inflammation marker in one category may negate the score of having no inflammatory markers in another marker category. It is important to note that the inflammation machine-learning model 124 may train using a large quantity of inflammation marker ranges depending on input user inflammation markers.

Continuing in reference to FIG. 1, computing device 104 identifies, as a function of the inflammation metric, at least an alimentary element for reversing inflammation in the user. An "alimentary element," as used in this disclosure, is a food item, supplement, nutrient, or a combination thereof that a person may eat, take, or otherwise consume. An alimentary element 128 may be a food item such as a fruit, vegetable, or dairy product; alternatively or additionally an alimentary element may be a spice, cooking ingredient, probiotic, or the like, such as echinacea, onion powder, oils such as avocado oil and mineral oil, plant extracts such as vanilla extract, wintergreen extract, probiotics, and the like. Alimentary element 128 may be a macronutrient or supplement such as branched chain amino acids (BCAAs), proteins such as whey protein, casein protein, enzymes such as lipase, carbohydrates such as dietary fiber and inulin, among other dietary supplements. An alimentary element 128 may be considered a complete meal or food item that can be consumed on its own, and/or as an ingredient or component of a dish and/or meal, wherein the ingredient may require preparation or is intended to be used with a plurality of alimentary elements.

Continuing in reference to FIG. 1, computing device 104 determining the at least an alimentary element 128 for the user may include using the computing device 104 to query for a suitable alimentary element 128 for reversing inflammation in the user as a function of the at least an inflammation marker. A "suitable alimentary element," as used in this disclosure, is an alimentary element for reversing inflammation in the user, where the alimentary element does not negatively impact the user, for instance by triggering an allergy as determined from physiological extraction. Computing device 104 may query for a suitable alimentary element by accepting an input of the user inflammation level as a guide to query for alimentary elements that may reduce the inflammation metric of a user. Computing device 104 may query using an online internet web browser, peer-reviewed research, medical journals, clinical research, expert submission, SQL server, relational database, or the like, as described in further detail below. Computing device 104 may generate an output of alimentary elements for reversing inflammation in specific metrics of a user after a query related to the inflammation metric of the user. Persons skilled in the art, upon review of this disclosure in full, will be aware of the various ways in which a computing device may query sources of information using textual submission.

Continuing in reference to FIG. 1, computing device 104 querying for a suitable alimentary element 128 may include using the alimentary element machine-learning process to retrieve at least a recipe for the suitable alimentary element 128, wherein the recipe reduces the at least an inflammation marker. A "recipe," as used in this disclosure, is a series of steps and/or instructions regarding a list of ingredients and methods for preparing a meal using the indicated ingredients. Computing device 104 querying for an alimentary element 128 for reversing the inflammation metric 120 of user may include locating and retrieving a recipe 132 for using an alimentary element 128, wherein all elements—including ingredients, cooking oils, spices, and the like—are compatible with a user's inflammation metric 120. An alimentary element machine-learning process may be any suitable machine-learning algorithm or process that may be performed by a machine-learning module, as described in further detail below. Computing device 104 may query for the recipe in the same manner as querying an alimentary element 128; alternatively or additionally computing device 104 may use the alimentary element machine-learning process 136 to query and retrieve recipe 132. Alimentary element machine-learning process 136 may accept an input of a plurality of alimentary elements 128 that were previously queried to build, construct, or otherwise generate a recipe using the alimentary elements 128. Alimentary element machine-learning process 136 may accept an input that is a single alimentary element 128 and retrieve recipes including additional alimentary elements, cross-checking each individual ingredient for its potential effect on inflammation metric 120, wherein additional alimentary elements that may contribute to inflammation may be swapped, or otherwise changed to either a new alimentary element, or omitted from the recipe. Alimentary elements 128 and/or recipes 132 compatible with a user inflammation metric 120 may be stored and/or retrieved by the alimentary element machine-learning process from a database, as described in further detail below, wherein the machine-learning process learns what options are best for an individual.

Continuing in reference to FIG. 1, computing device 104 provides a representation of the at least an alimentary element 128 for reversing inflammation within a graphical user interface. Computing device 104 may be a user device. User device may be any device suitable for displaying text, graphics, and the like, such as a "smartphone", laptop, or any other suitable device. User device may be interactive wherein user device may display a suggestion and a user may select or input information based upon the suggestion. User device may provide a representation of the at least an alimentary element 128 to the user within a graphical user interface (GUI), wherein the GUI may display text, graphics, metrics, or any other outputs generated by system 100. Persons skilled in the art, upon review of this disclosure in its entirety, will be aware of the various device that may be suitable as a user device and the various methods of displaying alimentary elements, recipes, inflammation metrics, and the like via graphical user interface.

Continuing in reference to FIG. 1, computing device 104 providing to the user the at least an alimentary element 128 for reversing inflammation may include conveying the at least an alimentary element amount to a user device and receiving a user input from the user device. Computing device 104 may communicate an amount of the alimentary element 128 for reversing inflammation, wherein the amount is a minimal quantity for the anti-inflammatory effect. In non-limiting illustrative examples, an amount may be a single serving, for instance a piece of fruit, such as an apple. In other non-limiting illustrative examples, an amount may be a total mass, a dosage, frequency, or the like, for instance where the alimentary element 128 is a supplement. User device may receive, from a user, an input. An input may be a user selecting an alimentary element 128 so that system 100 may know how the user's inflammation metric 120 will change. An input received from a user may be an alimentary element the user intends to consume, wherein system 100 may suggest an alternative alimentary element 128.

Computing device 104 receiving a user input may receive, from the user device, a first alimentary element and determine, using the inflammation machine-learning model 124 and the first alimentary element, the effect of the first alimentary element on the inflammation metric 120 of the user; and generating an inflammatory response label as a function of determining the affect. An "inflammatory response label," as used in this disclosure is a label indicating a qualitative and/or quantitative effect on an inflammatory metric 120 that can be determined for a food item, meal, supplement, or the like, consumed by a user. In non-limiting illustrative examples, inflammation machine-learning model may accept an input of a first alimentary element and an inflammation metric 120, determine an output that describes how at least an inflammation marker, and thus inflammation metric 120, is affected by a first alimentary element. Such an output may be an inflammatory response label 140. An inflammatory response label 140 may be a predictive measure of how a first alimentary element may affect a user's inflammation. An inflammatory response label 140 may be a numerical value such as a percent of change due to a first alimentary element, wherein the percent change may be from a one-time use of the alimentary element, from sustained used over time, or any other pattern of use indicated by a user.

Continuing in reference to FIG. 1, computing device 104 may be configured to receive a plurality of inflammation metrics, establish at least an alimentary element for reversing inflammation in the plurality of inflammation measurements, generate, by querying a database, at least a recipe for the plurality of alimentary components that do not contribute to inflammation in the plurality of inflammation measurements, and provide, to the user, the recipe. As used herein, "plurality of inflammation metrics" refers to a plurality of inflammation metrics, wherein there may be a plurality of individuals, each with an inflammation metric. In such an instance, computing device 104 may accept an input of the plurality of inflammation metrics and generate an output which is a recipe, wherein the recipe contains alimentary elements that reduce the plurality of inflammation metrics of the individuals. In non-limiting exemplary embodiments, computing device 104 may use the alimentary element machine-learning process 136 to query for and retrieve alimentary elements that may reduce the inflammation metrics of each person, removing alimentary elements that may contribute to inflammation in a person. Computing device 104 may query a database for the alimentary elements, as described in further detail below. The alimentary element machine-learning process 136 may then compile a list of alimentary elements that reduce inflammation of at least an inflammation metric, and also do not contribute to increasing inflammation in any individual, and then query for at least a recipe that uses the alimentary elements, as described above for a single user.

Computing device 104 using the alimentary element machine-learning process 136 may use inflammation machine-learning model 124 to determine how each alimentary element will affect the inflammation markers of a user, and thus the inflammation metric. Computing device 104 may store and/or retrieve recipes, alimentary elements, inflammation metrics, inflammation markers, heuristics, relationships, and other qualitative and quantitative data in determining recipes for a plurality of inflammation metrics. Computing device 104 may provide, to the user, the recipe via a user action, as described in further detail below.

Continuing in reference to FIG. 1, computing device 104 may receive user data, wherein user data may be more current in time than a first provided alimentary element and contains at least an alimentary element selected by the user, generate, using the inflammation machine-learning model and the user data, a second inflammation metric. "User data" as used herein is any alimentary element and/or recipe a user has input via a user device, wherein the data was input by the user after a first inflammation metric was provided to the user. Additionally, user data may include any physiological extraction data of a user more recent than a first physiological extraction datum provided by the user. Computing device 104 may generate using the inflammation machine-learning model trained to recognize correlations between alimentary elements and inflammation markers in a user and determine a second inflammation metric. Computing device 104 may accept inputs of updated user data 144 and retrieve a first inflammation metric 120 of a user and generate an output which is a second inflammation metric 148, wherein the second inflammation metric 148 reflects any changes in inflammation due to alimentary elements consumed by a user. Alternatively or additionally, computing device 104 may retrieve from a database an applicable inflammatory response label 140 associated with the alimentary element to assist in generating the second inflammation metric 148. Computing device 104 may display to a user, via a user device, the second inflammation metric 148, as described above. Computing device 104 may store and/or retrieve a second inflammation metric 148 from a database, as described in further detail below.

Continuing in reference to FIG. 1, computing device 104 may calculate a numerical difference between a first inflammation metric 120 and a second inflammation metric 148. Computing device 104 may calculate a numerical difference using any suitable mathematical operation, for instance and without limitation, using subtraction. Computing device 104 may calculate a quantitative difference, wherein the difference is a numerical value between two inflammation metrics, for instance wherein the inflammation metrics may differ from changes in diet, changes in time, and the like. Alternatively or additionally, computing device 104 may calculate a quantitative difference wherein the difference is a mathematical expression such as a function, vector, polar coordinate, matrix of values, or the like, wherein the expression describes, for instance and without limitation, a difference between rates of inflammation change between two or more inflammation metrics. In such an example, computing device 104 may inform a user how the inflammation metrics have changed over a longer period of time, wherein a plurality of inflammation metrics has been calculated using a plurality of past user data inputs.

Continuing in reference to FIG. 1, determining the quantitative difference between the first inflammation metric and the second inflammation metric may include determining, using a ranking machine-learning process, if a quantitative difference in inflammation metric is due to changes in changes in user indicated alimentary elements. Ranking machine-learning process may be implemented using any type of machine-learning process and/or algorithm suitable for use as the alimentary element machine-learning process 136. Ranking machine-learning process may be any type of machine-learning process and/or algorithm that may be performed by a machine-learning module, as described in further detail below. Ranking machine-learning process 152 may accept inputs that are quantitative differences between two or more inflammation metrics of a user and determine if the difference is due to an indicated alimentary element, as opposed to a difference due to physiological extraction data. In doing so, ranking machine-learning process 152 may learn which alimentary elements resulted in reduced and/or reversed inflammation in a user.

Continuing in reference to FIG. 1, computing device 104 may catalogue alimentary elements present in the user data that resulted in decreases in inflammation metric, wherein cataloguing includes saving a list 156 of selected alimentary components in a database for a user. In non-limiting exemplary embodiments, cataloguing alimentary elements in this way saves a list 156 of beneficial alimentary elements a user has indicated that he or she preferably consumes and/or uses in recipes. In non-limiting illustrative examples, computing device 104 may recognize user food preferences, predict potential food allergies, hypersensitivities, gut wall interaction, and the like, based on user consumption patterns from the catalogued foods. For instance and without limitation, if a pattern emerges wherein meals and/or foods with gluten, wheat, flour, and the like, result in unusual increases in inflammation, yet a user continues to consume these alimentary elements, computing device 104 may alert a user with inflammation response labels 140 that indicate potential for conditions such as rheumatoid arthritis (RA), celiac disease, gluten intolerance, and the like, and/or suggestions for alimentary elements to replace the items. Alternatively or additionally in non-limiting examples, if a user prefers to eat berries, such as blueberries, blackberries, and raspberries, but not strawberries, computing device 104 may catalogue those alimentary elements in a list 156, and predict that a user abstains from strawberries due to an allergy, and may learn not suggest alimentary elements or recipes that use strawberries.

Continuing in reference to FIG. 1, ranking machine-learning process 152 determining the quantitative difference between the first inflammation metric and the second inflammation metric may include ranking, using the catalogued list, a plurality of alimentary components based on their effect on the user inflammation metric In non-limiting exemplary embodiments, ranking machine-learning process 152 may accept an input of catalogued alimentary elements, and generate a ranked list 160 as an output, wherein generating the ranked list 160 includes use a ranking algorithm to rank alimentary elements based on their impact on reversing inflammation. Ranking may be performing using a ranking process, as described in further detail below.

Still referring to FIG. 1, in some embodiments, system 100 may receive a plurality of physiological extractions 108 of a subject. In some embodiments, one or more physiological extractions 108 may include an inflammation metric. Physiological extractions and inflammation metrics are described above.

Still referring to FIG. 1, in some embodiments, system 100 may receive a plurality of alimentary element consumption data. As used herein, "alimentary element consumption data" is data describing an alimentary element a subject has eaten, taken, or otherwise consumed. Alimentary element consumption data may further include, in non-limiting examples, data describing how much of an alimentary element was consumed, and/or when the alimentary element was consumed. In some embodiments, alimentary element consumption data may include when an alimentary element was consumed relative to a time at which a physiological extraction is measured. In some embodiments, alimentary element consumption data may describe consumption of a single alimentary element or type of alimentary element. This may, for example, aid in measuring effects of an alimentary element in isolation. In some embodiments, alimentary element consumption data may describe consumption of a plurality of alimentary elements or types of alimentary elements. This may, for example, improve reliability of data by making data collected more closely resemble contexts in which alimentary elements may be consumed outside of a testing environment.

Still referring to FIG. 1, in some embodiments, alimentary element consumption data may describe an alimentary element a subject has eaten, taken, or otherwise consumed prior to a physiological extraction. In some embodiments, alimentary element consumption data may describe an alimentary element a subject has eaten, taken, or otherwise consumed at least 5 minutes, 10 minutes, 15 minutes, 30 minutes, 1 hour, 2 hours, 3 hours, 4 hours, 5 hours, 6 hours, 7 hours, 8 hours, 9 hours, 10 hours, 12 hours, 18 hours, 24 hours, or 48 hours prior to a physiological extraction. In some embodiments, alimentary element consumption data may describe an alimentary element a subject has eaten, taken, or otherwise consumed within 5 minutes, 10 minutes, 15 minutes, 30 minutes, 1 hour, 2 hours, 3 hours, 4 hours, 5 hours, 6 hours, 7 hours, 8 hours, 9 hours, 10 hours, 12 hours, 18 hours, 24 hours, or 48 hours prior to a physiological extraction. In some embodiments, alimentary element consumption data may describe an alimentary element a subject has eaten, taken, or otherwise consumed within a time frame where inflammatory effects of consumption of an alimentary element are present and/or are at a peak.

Still referring to FIG. 1, in some embodiments, receiving a plurality of alimentary element consumption data may include tracking subject's historical consumptions of one or more alimentary elements with a set of predetermined alimentary elements. For example, alimentary elements may be pre-prepared with known compositions, subjects may consume such alimentary elements, and physiological extractions may subsequently be collected from subject. In some embodiments, tracking subject consumption of alimentary elements with predetermined ingredients may improve reliability of alimentary element consumption data. In some embodiments, system 100 may receive a plurality of alimentary element consumption data describing, for each alimentary element consumption datum of the plurality of plurality of alimentary element consumption data, consumption of the subject prior to a physiological extraction of the plurality of physiological extractions.

Still referring to FIG. 1, system 100 may generate one or more instances of alimentary element compatibility data. As used herein, an "alimentary element compatibility datum" is a datum describing a degree to which an alimentary element causes an inflammatory response in a subject. In some embodiments, an alimentary element compatibility datum may include a prediction and/or estimate as to a degree to which an alimentary element causes an inflammatory response in a subject. System 100 may generate one or more instances of alimentary element compatibility data using an alimentary element compatibility machine learning model. Alimentary element compatibility machine learning model may be trained using a supervised learning algorithm. Alimentary element compatibility machine learning model may include, for example, a classifier. Alimentary element compatibility machine learning model may be trained on a training dataset including a plurality of example physiological extractions and a plurality of example alimentary element consumption data, associated with example alimentary element compatibility data. Such a training dataset may be obtained from, for example, a third party database including historical inflammation marker measurements of subjects, and historical severity of inflammatory symptoms. Once alimentary element compatibility machine learning model is trained, it may be used to determine alimentary element compatibility data. System 100 may input physiological extraction and/or alimentary element consumption datum into alimentary element compatibility machine learning model, and apparatus 100 may receive alimentary element compatibility data from the model. Such physiological extraction may include inflammation metric. In some embodiments, alimentary element compatibility machine learning model may include a classifier trained to categorize inputs such as alimentary element consumption data to categories representing severity of inflammatory response. For example, inputs may be categorized into categories associated with "mild", "moderate" or "severe" inflammatory responses, or no inflammatory response. Alimentary elements which subjects consumed within a time frame prior to an input physiological extraction may be categorized into categories as dictated by classifier output.

Still referring to FIG. 1, in some embodiments, each alimentary element compatibility datum of a plurality of alimentary element compatibility data is associated with at least an alimentary element consumption datum of the plurality of alimentary element consumption data. In some embodiments, each alimentary element consumption datum of a plurality of alimentary element consumption data is associated with at least physiological extraction of a plurality of physiological extractions. An association between one or more of an alimentary element consumption datum, a physiological extraction, and a compatibility datum may enable a computing device to link compatibility data indicating levels of inflammation with alimentary elements described by alimentary element consumption data. In some embodiments, this connection is made based on both such elements of data being associated with the same physiological extraction. In some embodiments, a physiological extraction is associated with an alimentary element consumption datum based on a relative timing of a physiological extraction measurement, and alimentary element consumption as described herein.

Still referring to FIG. 1, in some embodiments, system 100 may identify an inflammatory alimentary element. As used herein, an "inflammatory alimentary element" is an alimentary element which causes a measurable inflammatory response in a subject consuming the alimentary element. In some embodiments, inflammatory alimentary element may include selecting an instance of alimentary element consumption data, where that instance of data describes consumption of the subject prior to a physiological extraction which alimentary element compatibility machine learning model categorizes as above a predetermined threshold of inflammatory effect. In some embodiments, an inflammatory alimentary element may include an alimentary element which is more inflammatory than 1%, 5%, 10%, 20%, 30%, 40%, 50%, 60%, 70%, 80%, 90%, 95%, 99%, or more of other alimentary elements. In some embodiments, such other alimentary elements may include other tested alimentary elements. In some embodiments, such other alimentary elements may include other alimentary elements according to estimated consumption by a population.

Still referring to FIG. 1, in some embodiments, each alimentary element consumption datum of a plurality of alimentary element consumption data is associated with an alimentary element compatibility datum of a plurality of alimentary element compatibility data. Such associations are based on timing of consumption of alimentary elements of alimentary element consumption data, and physiological extractions whose data is input into alimentary element compatibility machine learning model in order to generate alimentary element compatibility datum. In some embodiments, identifying an inflammatory alimentary element may include generating an alimentary element compatibility representation by categorizing alimentary element consumption data according to the associated alimentary element compatibility data. As used herein, an "alimentary element compatibility representation" is a representation of data describing an alimentary element and a degree to which the alimentary element causes inflammation in a subject, in a form suitable for presentation to a user. Such a user may include, in non-limiting examples, a subject and/or a medical professional. Alimentary element compatibility representation may include, in non-limiting examples, a table, chart, list, or graph identifying one or more alimentary elements and associated inflammatory effects. For example, alimentary element compatibility representation may include a table listing a variety of alimentary elements, and how inflammatory each listed alimentary element is, or is predicted to be, to the subject. In some embodiments, alimentary element compatibility representation may include one or more predictions as to inflammatory effects of alimentary elements.

Still referring to FIG. 1, in some embodiments, system 100 may transmit to a remote device operated by a subject alimentary element compatibility representation. In some embodiments, system 100 may receive from a remote device operated by a subject an alimentary element annotation. As used herein, an "alimentary element annotation" is a datum including language input by a user viewing an alimentary element compatibility representation. In non-limiting examples, alimentary element annotations may include notes on types of alimentary elements and their associated inflammatory levels, or questions a user has for a medical professional. In another non-limiting example, alimentary element annotations may include subject preferences as to alimentary elements for reasons other than inflammatory effect, such as health benefits, caloric density, taste, cost, ease of preparation, and the like. System 100 may store an alimentary element annotation. System 100 may transmit an alimentary element annotation to a remote computing device, such as a remote computing device operated by a subject, or a remote computing device operated by a medical professional. Such a data transmission may be performed when, for example, such a remote device requests alimentary element annotation. Transmission of alimentary element annotations to a remote device operated by a medical professional may aid the medical professional in making dietary recommendations to a subject. For example, a medical professional may take into account both inflammatory effects, and information in alimentary element annotations, such as subject preferences on alimentary elements for reasons other than inflammatory effects.

Still referring to FIG. 1, in some embodiments, alimentary element compatibility representation may be presented using a graphical user interface (GUI). In some embodiments, alimentary element compatibility representation may include one or more interactive components. In some embodiments, system 100 may receive from a remote device operated by a subject an alimentary element selection. As used herein, an "alimentary element selection" is a datum describing an interaction between a user and alimentary element compatibility representation. In a non-limiting example, a user may interact with alimentary element compatibility representation using a touchscreen button, and a tooltip may appear describing in more detail an element selected by the user.

Still referring to FIG. 1, in some embodiments, system 100 may update alimentary element compatibility representation. For example, system 100 may receive a subsequent physiological extraction of a subject, wherein the subsequent physiological extraction includes an inflammation metric; receive a subsequent alimentary element consumption datum describing consumption of the subject prior to the subsequent physiological extraction; generate a subsequent alimentary element compatibility datum for the subsequent alimentary element consumption datum by generating the subsequent alimentary element compatibility datum as a function of the subsequent physiological extraction using the trained alimentary element compatibility machine learning model; update the alimentary element compatibility representation as a function of the subsequent alimentary element compatibility datum; and transmit to the remote device operated by the subject the updated alimentary element compatibility representation.

Still referring to FIG. 1, in some embodiments, system 100 may identify one or more inflammatory alimentary elements as a function of alimentary element compatibility data and/or previously identified inflammatory alimentary elements. For example, upon identifying a first inflammatory alimentary element, system 100 may identify a second alimentary element and/or an alimentary element category which is commonly an inflammatory alimentary element in individuals in which the first inflammatory alimentary element is inflammatory. In a non-limiting example, if individuals which have inflammatory responses to cashews commonly also have inflammatory responses to almonds, than almonds may be identified as an inflammatory alimentary element if cashews are identified as an inflammatory alimentary element. In some embodiments, a machine learning model may be used to identify groups of individuals which respond similarly to alimentary elements and/or groups of alimentary elements which individuals respond similarly to. Machine learning models suitable for such grouping tasks are described further herein.

Still referring to FIG. 1, in some embodiments, system 100 may pair a medical professional with a subject as a function of inflammatory alimentary element. In some embodiments, pairing a medical professional with a subject includes identifying a medial professional with experience providing guidance as to health effects of alimentary elements of a category including the inflammatory alimentary element. In some embodiments, pairing a medical professional with a subject may include collecting identifying information of a subject, and transmitting the identifying information of the subject to the medical professional. In some embodiments, pairing a medical professional with a subject may include collecting identifying information of a medical professional, and transmitting the identifying information of the medial professional to the subject. Identifying information may include, in non-limiting examples, a name, phone number, email address, account number (such as an account number on a messaging platform), and a social media account handle. In some embodiments, pairing a medical professional with a subject may include opening a communication channel between the medial professional and the subject, such as by starting a phone call between the two. In some embodiments, pairing a medical professional with a subject may include scheduling a meeting including the medial professional and the subject. In some embodiments, a medial professional may be paired with more than one subject. For example, in some embodiments, two or more subjects may have similar inflammatory alimentary elements, and a medial professional may be paired with more than one such subject. A medical professional may include an artificial intelligence system including any simulation of human intelligence and/or problem-solving capabilities processed by a machine, such as a computer system.

Still referring to FIG. 1, in some embodiments, an inflammatory alimentary element may be displayed using a user interface of a display device. As used herein, a device "displays" a datum if the device outputs the datum in a format suitable for communication to a user. For example, a device may display a datum by outputting text or an image on a screen or outputting a sound using a speaker.

Figure 2:
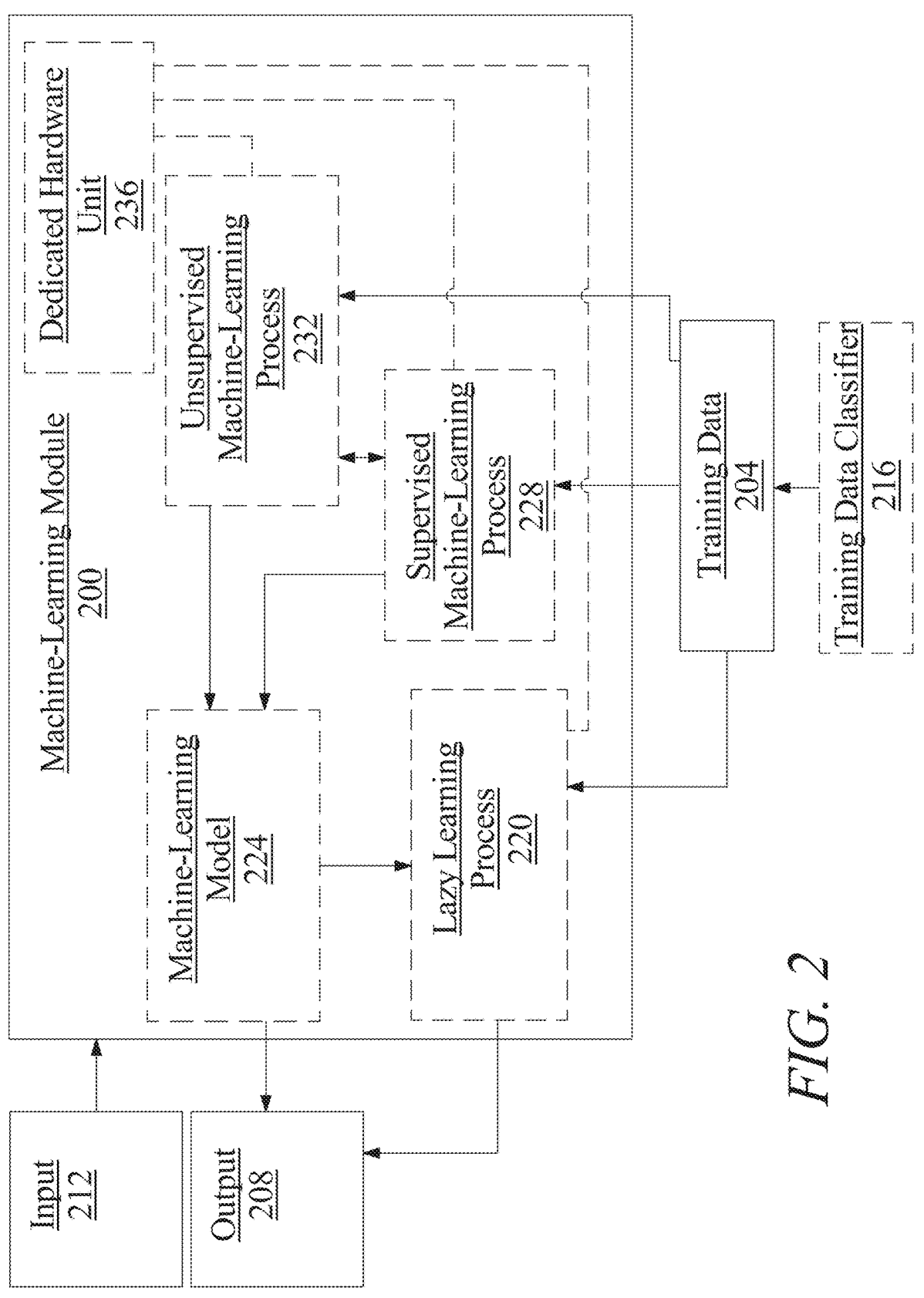
FIG. 2 is a block diagram of an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, inputs may include physiological extractions and outputs may include alimentary element compatibility data.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to categories of alimentary elements.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include physiological extractions as described above as inputs, alimentary element compatibility data as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 2, system 100 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 2, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; system 100 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Figure 3:
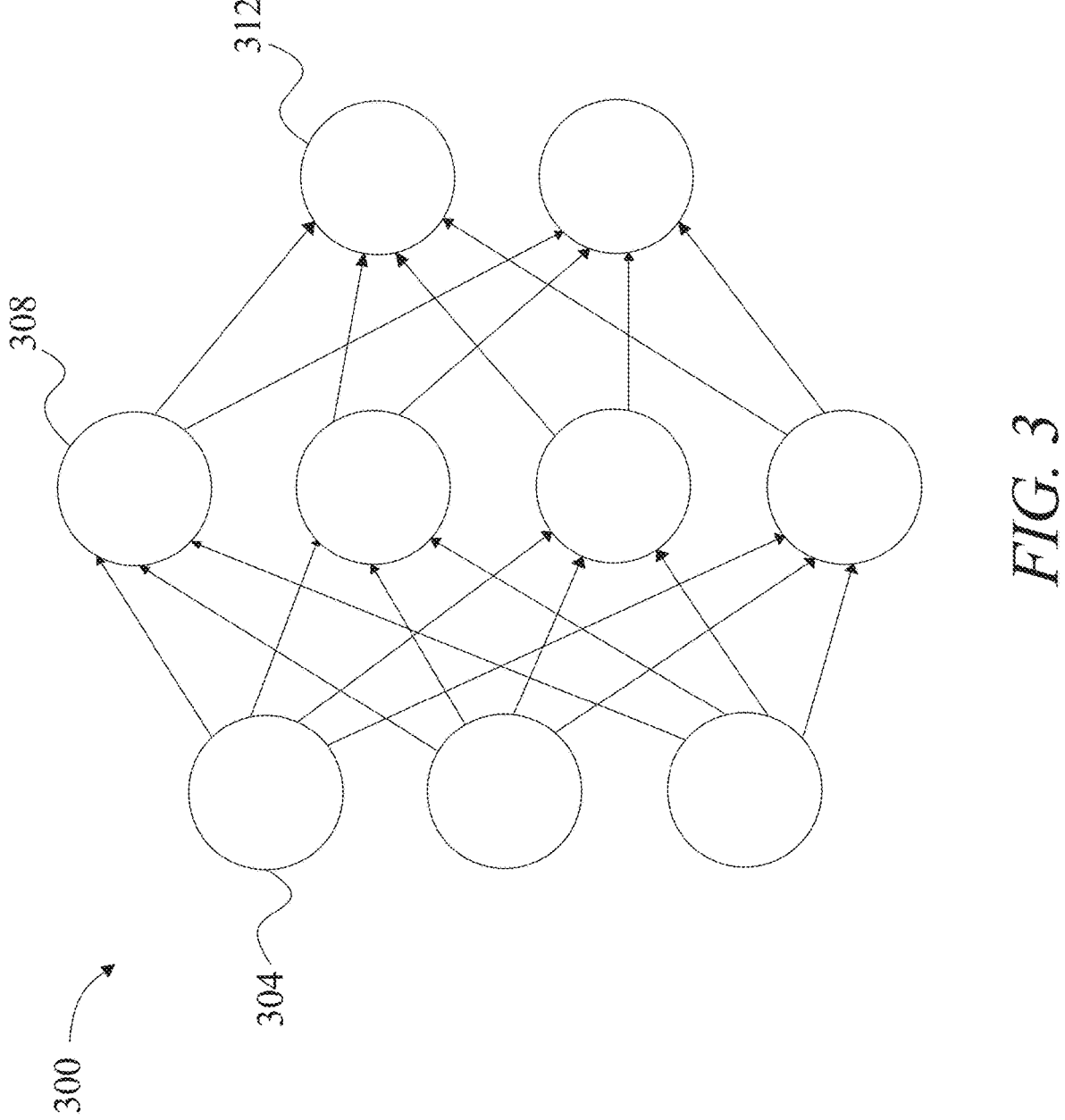
FIG. 3 is a block diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
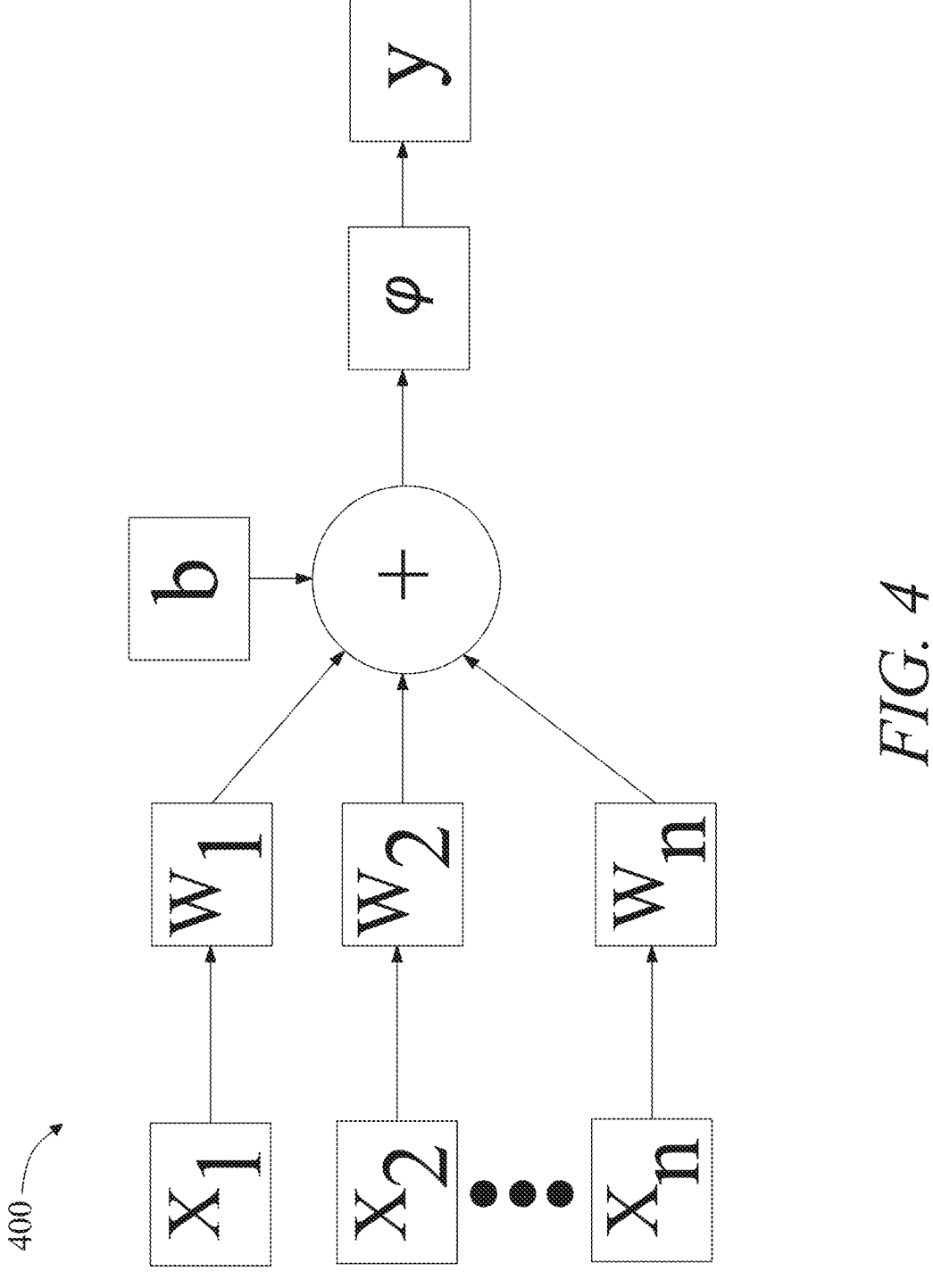
FIG. 4 is a block diagram of an exemplary embodiment of a neural network node.

Referring now to FIG. 4, an exemplary embodiment of a node 400 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x) = \tan h^2(x)$, a rectified linear unit function such as $f(x) = \max(0, x)$, a "leaky" and/or "parametric" rectified linear unit function such as $f(x) = \max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x*\text{sigmoid}(x)$, a Gaussian error linear unit function such as $f(x) = a(1 + \tan h($ $$\sqrt{2/\pi}$$

$(x + bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 4, a "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like. CNN may include, without limitation, a deep neural network (DNN) extension, where a DNN is defined as a neural network with two or more hidden layers.

Figure 5:
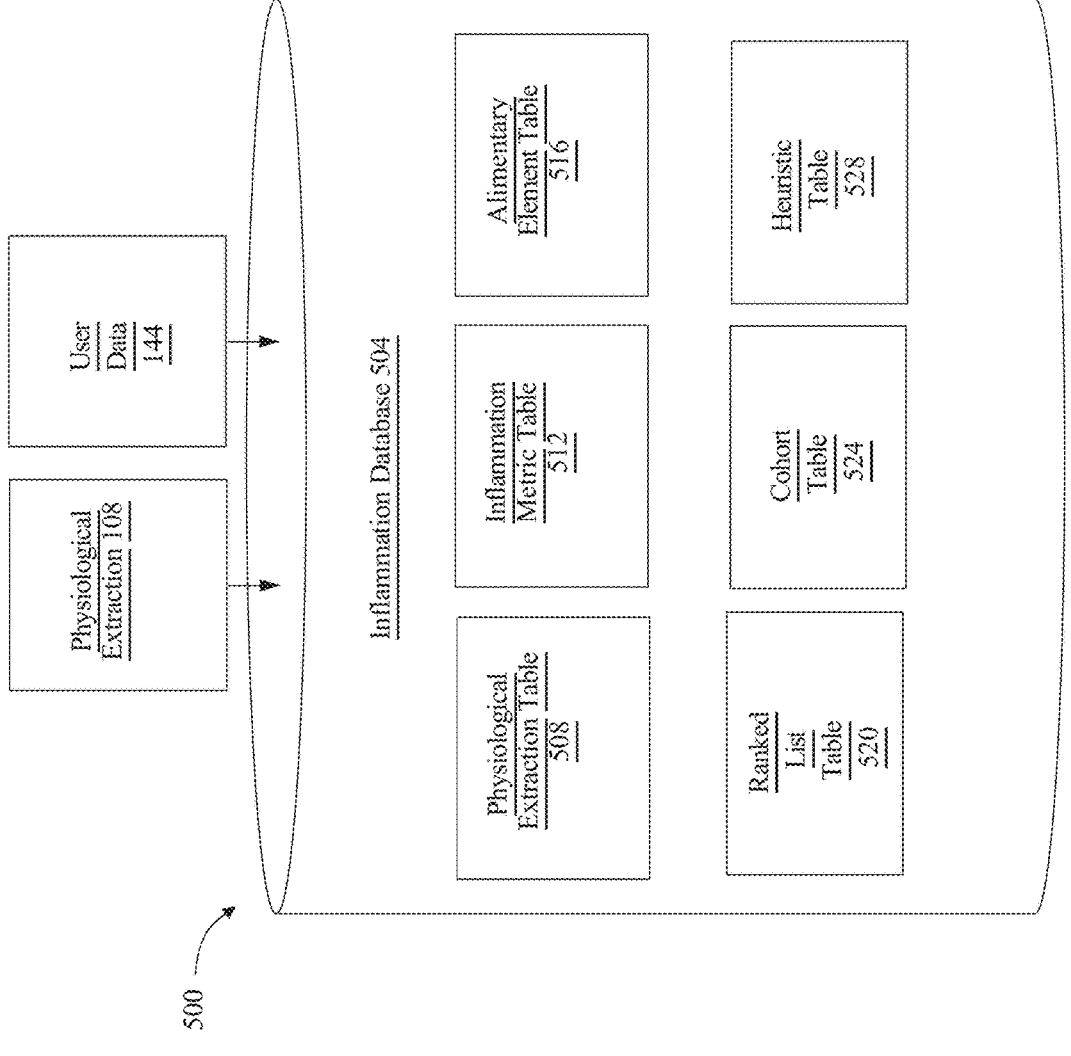
FIG. 5 is a block diagram of an exemplary embodiment of an inflammation database.

Referring now to FIG. 5, a non-limiting exemplary embodiment 500 of database is illustrated. A "database," as used herein may refer to an inflammation database 504. Inflammation database 504 may be implemented, without limitation, as a relational database, a key-value retrieval database such as a NOSQL database, or any other format or structure for use as a database that a person skilled in the art would recognize as suitable upon review of the entirety of this disclosure. Inflammation database 504 may alternatively or additionally be implemented using a distributed data storage protocol and/or data structure, such as a distributed hash table and the like. Inflammation database 504 may include a plurality of data entries and/or records, as described above. Data entries in a inflammation database 504 may be flagged with or linked to one or more additional elements of information, which may be reflected in data entry cells and/or in linked tables such as tables related by one or more indices in a relational database. Inflammation database 504 may be designated as an online repository of data, or other network-integrated data repository. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 5, inflammation database 504 may include, without limitation, a physiological extraction table 508, inflammation metric table 512, alimentary element table 516, ranked list table 520, cohort table 524, and/or heuristic table 528. Determinations by a machine-learning process, machine-learning model, scoring function, and the like, may also be stored and/or retrieved from the inflammation database 504, for instance in non-limiting examples a classifier describing a subset of users with alike physiological extraction data as it relates to inflammation. Determinations by a machine-learning model, for instance for calculating a degradation rate and/or a machine-learning process for determining an antidote strategy, may also be stored and/or retrieved from the inflammation database 504. As a non-limiting example, inflammation database 504 may organize data according to one or more instruction tables. One or more inflammation database 504 tables may be linked to one another by, for instance in a non-limiting example, common column values. For instance, a common column between two tables of inflammation database 504 may include an identifier of a submission, such as a form entry, textual submission, metrics, and the like, for instance as defined above; as a result, a query may be able to retrieve all rows from any table pertaining to a given submission or set thereof. Other columns may include any other category usable for organization or subdivision of expert data, including types of expert data, names and/or identifiers of experts submitting the data, times of submission, and the like; persons skilled in the art, upon reviewing the entirety of this disclosure, will be aware of various ways in which data from one or more tables may be linked and/or related to data in one or more other tables.

Still referring to FIG. 5, in a non-limiting embodiment, one or more tables of an inflammation database 504 may include, as a non-limiting example, a physiological extraction table 504, which may include elements of user physiological extraction 108 data, as described above, and any associated data relating to inflammation, determinations made by an expert, medical professional, physical trainer, or the like, including medical history data, physiological measurements, mental health, medical conditions, diagnoses, diseases, or any other factors for use in determining inflammation metrics 120, alimentary elements, and/or other elements of data computing device 104 may store, retrieve, and/or use to determine usefulness and/or relevance of physiological extraction 108 data in determining inflammation metrics 120, alimentary elements, and/or user efforts as described in this disclosure.

One or more tables may include, without limitation, inflammation metric table 512, which may include numerical values, functions, vectors, matrices, coordinates, graphical data, parameters, and the like, for instance and without limitation, that link user physiological extraction 108 to ranges of inflammation markers, inflammation metrics, and the like, as described above. Inflammation metric table 512 may contain physiological ranges of inflammation markers, including organization of inflammation markers based on classification as 'systemic' or 'local', as described above.

One or more tables may include, without limitation, alimentary element table 516, which may include alimentary elements, recipes, food items, restaurant menus, meals, and the like, including any associated physiological extraction 108 data. In non-limiting illustrative examples, alimentary element table 516 may include alimentary elements that are organized according to when a user input the data, including for instance timestamps, amounts, and the like, associated with when and how a user consumed the alimentary element.

One or more tables may include, without limitation, a ranked list table 520, which may correlate user alimentary elements to influence an inflammation metric as it pertains to a determinations about inflammation metric 120, alimentary elements, recipes, and the like, including any outcomes, models, heuristics, scores and/or combinations thereof as they may correspond to rankings, determination, calculations, or combinations of catalogued items listed as numerical values, metrics, functions, vectors, matrices, and the like, that corresponds to determining a alimentary elements that may have been cached, catalogued, or otherwise stored.

One or more tables may include, without limitation, a cohort category table 524, which may contain one or more inputs identifying one or more categories of data, for instance demographic data, lifestyle data, physiological data, sleep pattern data, or the like, with regard to which users having matching or similar data may be expected to have similar inflammation metrics 120, alimentary elements, recipes, ranked lists, inflammation markers, or the like, as a result of a machine-learning process determination, machine-learning model, ranking algorithm, and/or other data input and output elements.

One or more tables may include, without limitation, a heuristic table 528, which may include one or more inputs describing potential mathematical relationships between at least an element of user data and, for instance and without limitation, physiological extraction 108 data, inflammation metrics 120, alimentary elements, inflammation markers, and the like, as a result of a machine-learning process determination, machine-learning model, ranking function, and the like, as described above.

Figure 6:
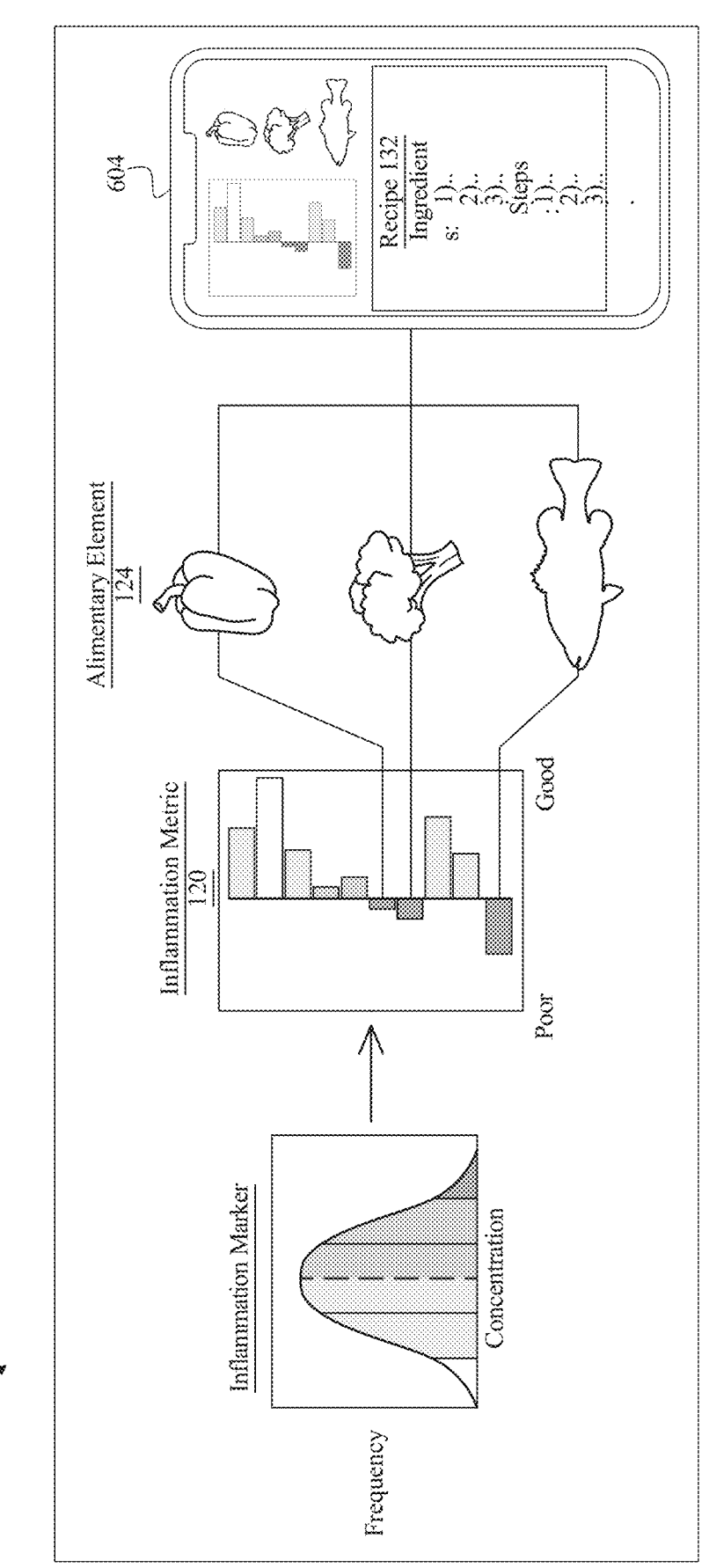
FIG. 6 is a diagrammatic representation of an exemplary embodiment for generating alimentary elements.

Referring now to FIG. 6, a non-limiting exemplary embodiment 600 of a workflow for generating alimentary elements 124 for reversing inflammation in a user. User physiological extraction 108 data may include data regarding an inflammation marker, such as a systemic inflammation marker 112 and/or a local inflammation marker 116. An inflammation machine-learning model 124 may determine a quantitative measure of a user's inflammation marker and assign an inflammation metric 120. In non-limiting illustrative examples, as shown in FIG. 6, there may be a normal distribution of concentration of an inflammation marker, such as IL-6, found in blood draws, wherein there is an equal distribution of frequency of concentrations about a mean value (denoted as the dashed line). In such an example, users may fall somewhere on the normal distribution wherein the machine-learning model may assign an inflammation metric 120 according to where the user falls, for instance highest score for lower concentration (white area under curve) to a lower score for higher concentrations of inflammatory marker (gradation of light grey to dark grey). For instance and without limitation, a user may have a quantitative measure that relates to a 'good', or healthy level of inflammatory marker, or 'poor', a higher level of an inflammatory marker that may signify a health concern. According to a user's inflammation metric 120, alimentary element machine-learning process 136 may identify at least an alimentary element 124 that can reverse inflammation in the user. These alimentary elements may be provided to a user, via a user device 604. In non-limiting illustrative examples, alimentary elements may be provided to reverse inflammation where there are indications of inflammation. Alternatively or additionally, alimentary elements may be suggested for swapping to 'better' alimentary element choices to prevent a 'good' inflammation metric 120 from getting worse.

Figure 7:
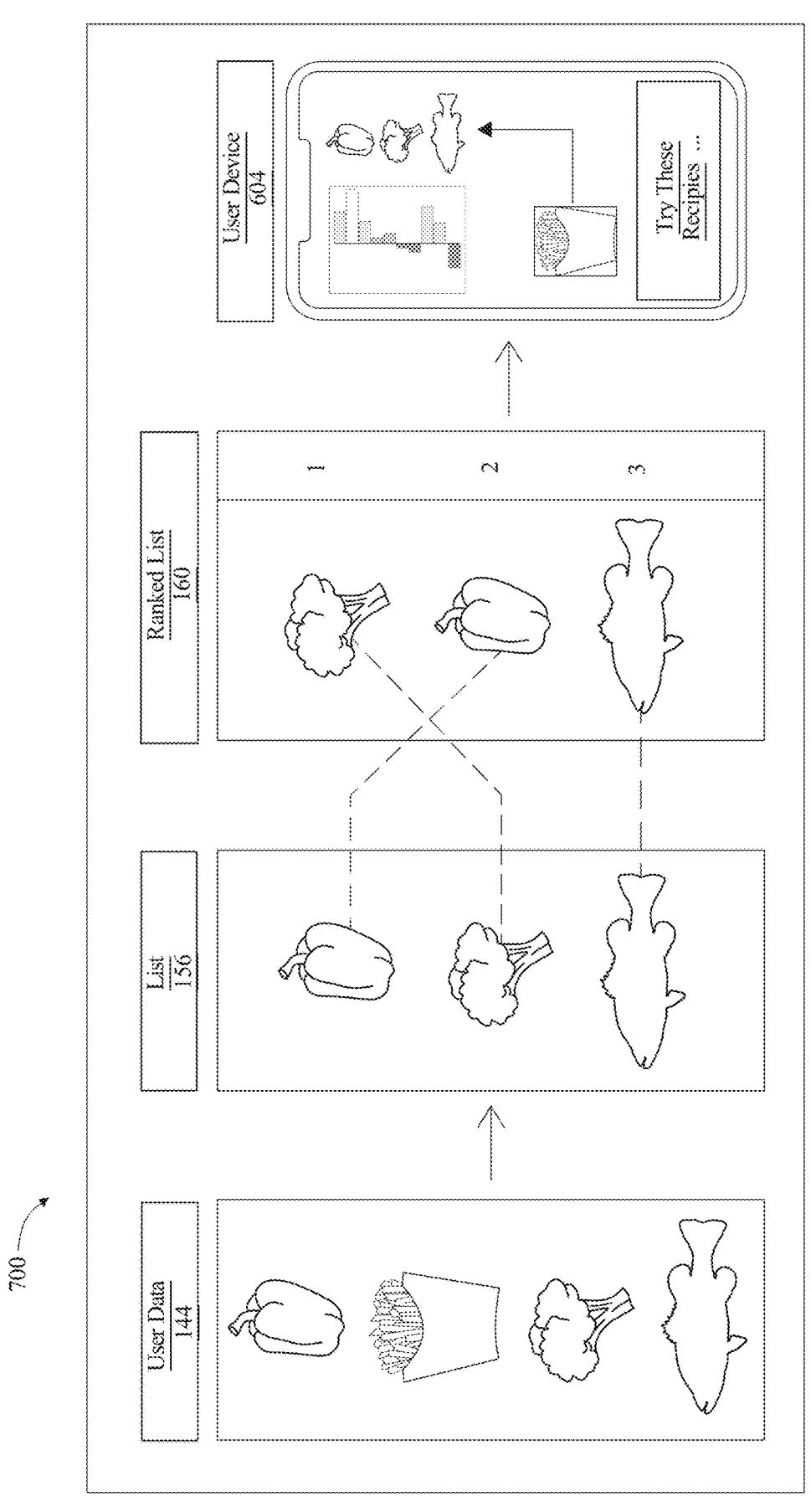
FIG. 7 is a diagrammatic representation of an exemplary embodiment of user data catalogued into a list to generate a ranked list.

Referring now to FIG. 7, a non-limiting exemplary embodiment 700 of user data 144 catalogued into a list 156 to generate a ranked list 160 to provide to a user device 404 is illustrated. User data 144 may be provided via a user device and/or retrieved from an inflammation database 504. Ranking machine-learning process 152 may catalogue a list 160 of alimentary elements based on the calculated effect of the alimentary elements on inflammation metric 120. Ranking machine-learning process 152 may use an inflammatory response label 140 to sort items into the list 156. Ranking machine-learning process 152 may generate a ranked list 160 of alimentary elements, wherein elements are ranked based on their effect on inflammation metric 120. Ranked list 160 may be provided via a user device so that a user may make an informed choice. Alternatively or additionally, computing device 104 may store and/or retrieve alimentary elements of the ranked list 160 and use the elements to identify and retrieve a recipe.

Figure 8:
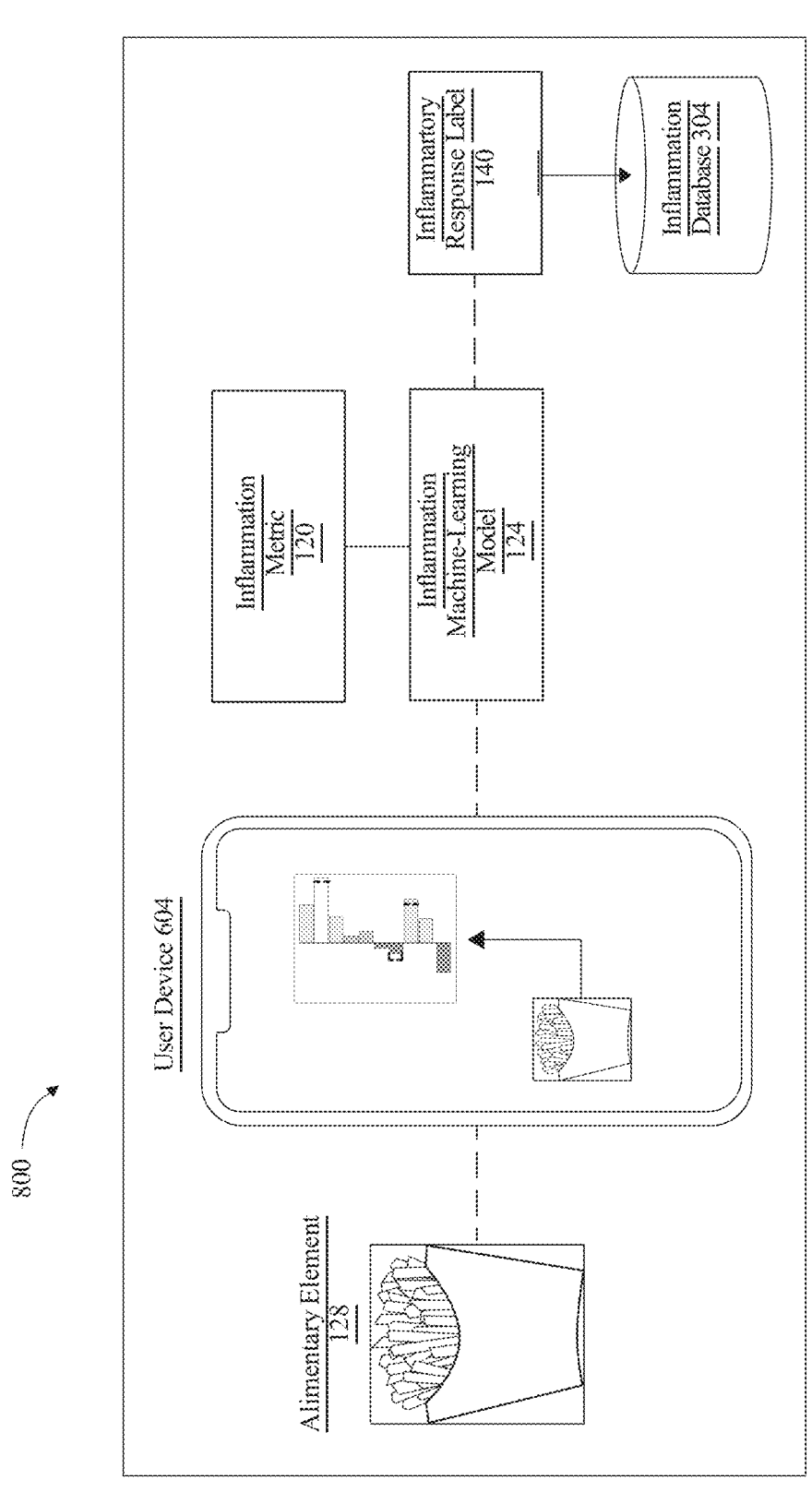
FIG. 8 is a diagrammatic representation of an exemplary embodiment of generating an inflammatory response label using an inflammation machine-learning model.

Referring now to FIG. 8, a non-limiting exemplary embodiment 800 of generating an inflammatory response label 140 using an inflammation machine-learning model 124 is illustrated. Inflammatory response label 140 may be a quantitative measurement of the inflammatory response a user may have to an alimentary element. A user may input an alimentary element via a user device 604, and the inflammation machine-learning model 124 may determine how this alimentary element will affect the inflammation metric 120. Such a process will result in an inflammatory response label 140 for that alimentary element for that user and may be stored and/or retrieved from an inflammation database 304.

Figure 9:
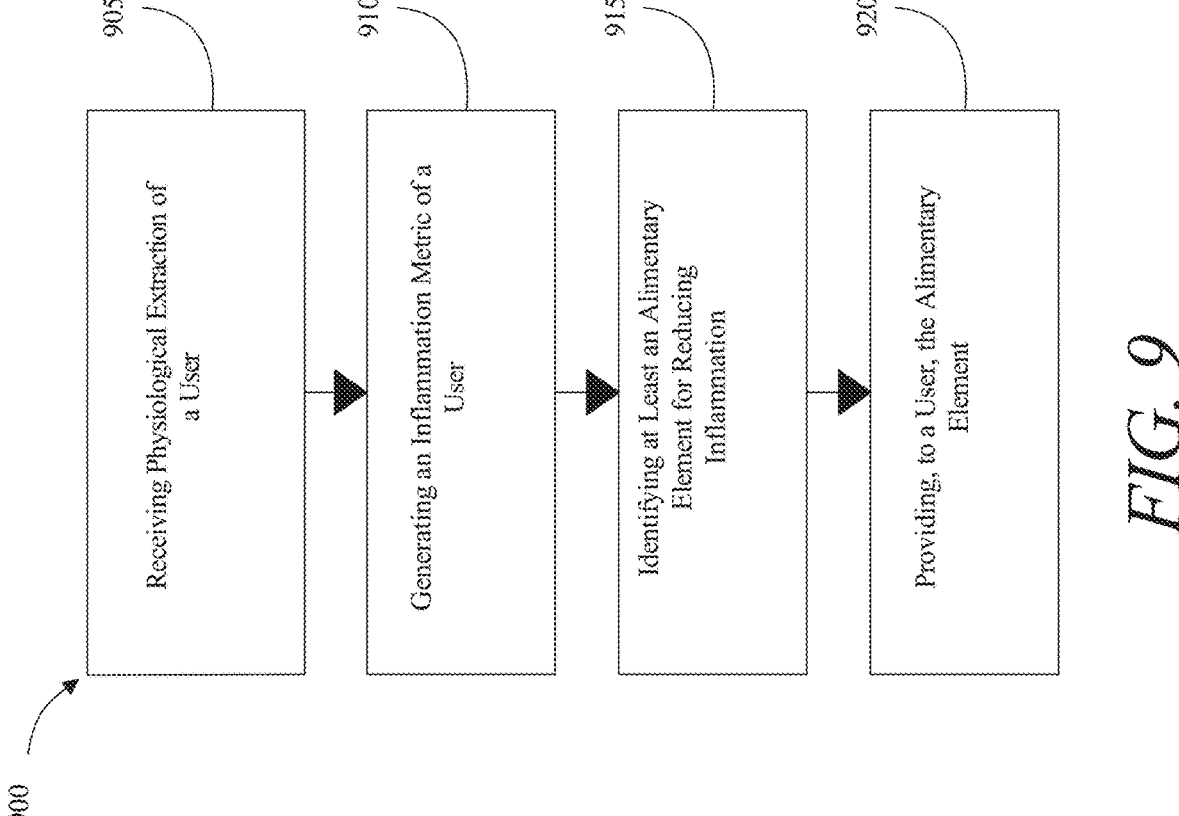
FIG. 9 is a flow diagram illustrating an exemplary workflow of a method for reversing inflammation in a user.

Referring now to FIG. 9, a non-limiting exemplary embodiment of a method 900 of reversing inflammation in a user is illustrated. At step 905, computing device 104 is configured for receiving physiological extraction 108 of a user, wherein physiological extraction 108 contains at least an inflammation marker. At least an inflammation marker further comprises a systemic inflammation marker 112. At least an inflammation marker further comprises a local inflammation marker 116; this may be implemented, without limitation, as described above.

At step 910, computing device 104 is configured for generating an inflammation metric 120 of a user, wherein generating the inflammation metric 120 may include using an inflammation machine-learning model 124, the inflammation machine-learning model 124 trained using training data 216 that enumerates hallmarks of inflammation in a user with quantitative measurements of inflammation; this may be implemented, without limitation, as described above.

At step 915, computing device 104 is configured for identifying, as a function of the inflammation metric 120 and an alimentary element machine-learning process 136, at least an alimentary element 128 for reversing inflammation in the user. Determining the at least an alimentary element 128 for the user may include querying for a suitable alimentary element 128 for reversing inflammation in the user as a function of the at least an inflammation marker. Querying for a suitable alimentary element 128 may include using the alimentary element machine-learning process 136 to identify at least a recipe 132 for the suitable alimentary element 128, wherein the recipe 132 reduces the at least an inflammation marker; this may be implemented, without limitation, as described above.

At step 920, computing device 104 is configured for providing, to the user, the at least an alimentary element 128 for reversing inflammation. Providing to the user the at least an alimentary element 128 for reversing inflammation may include conveying the at least an alimentary element 128 amount to a user device 304, and receiving a user input from the user device 304. Receiving, user input from the user device, may include a first alimentary element. Determining, using the inflammation machine-learning model 124 and the first alimentary element, the effect of the first alimentary element on the inflammation metric 120 of the user, and generating an inflammatory response label 140 as a function of determining the affect. Computing device 104 may be further configured to receive a plurality of inflammation measurements, establish at least an alimentary element for reversing inflammation in the plurality of inflammation measurements, and generate, by querying a database, at least a recipe for the plurality of alimentary components that do not contribute to inflammation in the plurality of inflammation measurements, and provide, to the user, the recipe. Computing device 104 may be further configured to receive user data 144, wherein user data 144 is more current in time than a first provided alimentary element 128 and contains at least an alimentary element selected by user, generate, using the inflammation machine-learning model 124 and the user data 144, a second inflammation metric, and calculate a quantitative difference between a first inflammation metric and a second inflammation metric. Determining the quantitative difference between the first inflammation metric and the second inflammation metric may include determining, using a ranking machine-learning process 152, if a quantitative difference in inflammation metric 120 is due to changes in user indicated alimentary elements, cataloguing alimentary elements present in the user data 144 that resulted in decreases in inflammation metric 120, wherein cataloguing includes saving a list of selected alimentary components in a database for a user, and ranking, using the ranking machine-learning process and the catalogued list, a plurality of alimentary components based on their effect on the user inflammation metric; this may be implemented, without limitation, as described above.

Figure 10:
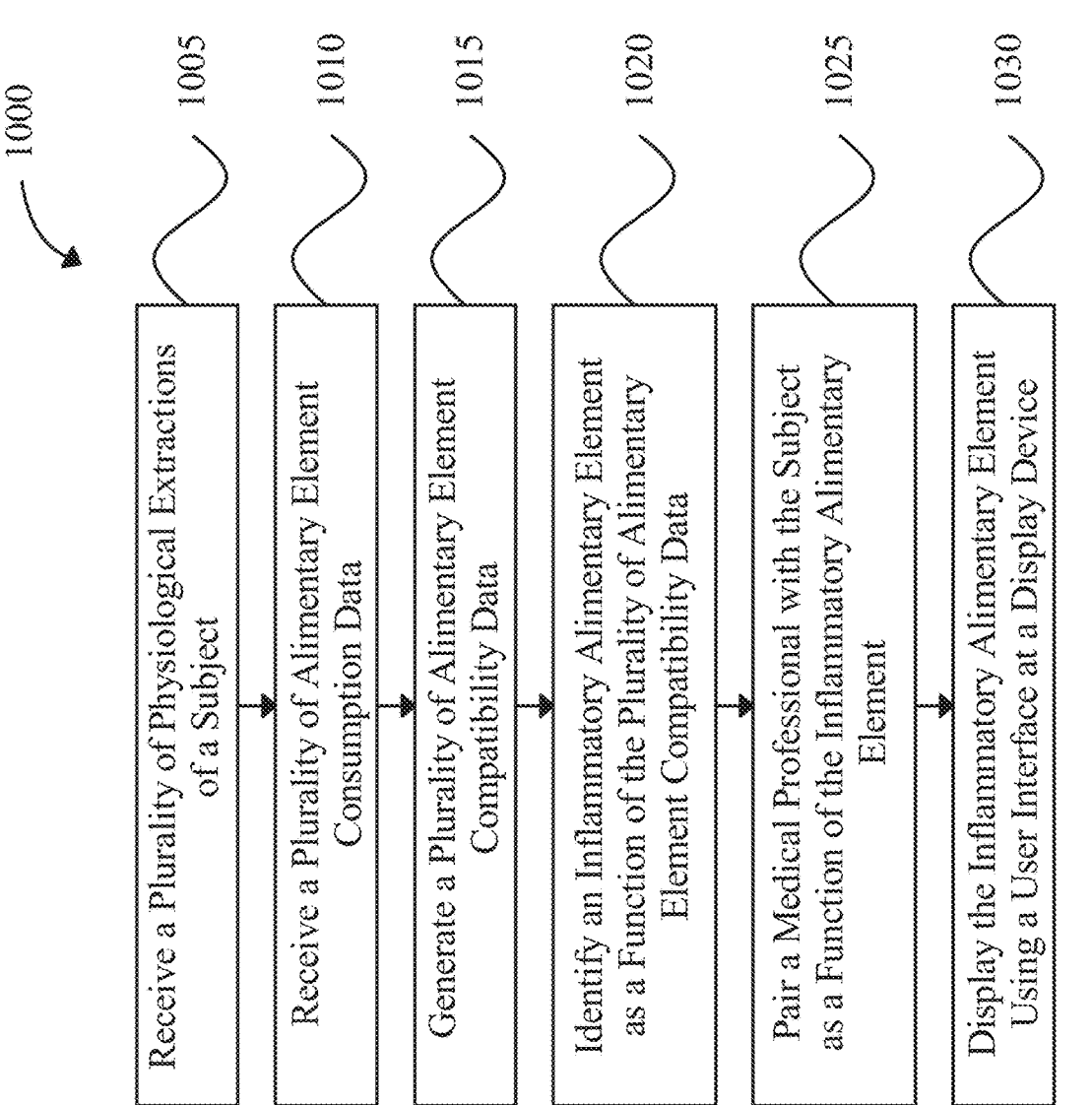
FIG. 10 is a flow diagram illustrating an exemplary method of generating a food compatibility datum.

Referring now to FIG. 10, an exemplary embodiment of a method 1000 of generating a food compatibility datum is illustrated. One or more steps if method 1000 may be implemented, without limitation, as described with reference to other figures. One or more steps of method 1000 may be implemented, without limitation, using at least a processor.

Still referring to FIG. 10, in some embodiments, method 1000 may include receiving a plurality of physiological extractions of a subject 1005. In some embodiments, plurality of physiological extractions comprises an inflammation metric.

Still referring to FIG. 10, in some embodiments, method 1000 may include receiving a plurality of alimentary element consumption data 1010. In some embodiments, the plurality of alimentary element consumption data may describe, for each alimentary element consumption datum of the plurality of plurality of alimentary element consumption data, consumption of the subject prior to a physiological extraction of the plurality of physiological extractions. In some embodiments, receiving the plurality of alimentary element consumption data comprises tracking subject consumption of alimentary elements with predetermined compositions.

Still referring to FIG. 10, in some embodiments, method 1000 may include generating a plurality of alimentary element compatibility data 1015. In some embodiments, generating the plurality of alimentary element compatibility data for the plurality of alimentary element consumption data may include training an alimentary element compatibility machine learning model on a training dataset including a plurality of example physiological extractions as inputs correlated to a plurality of example alimentary element compatibility data as outputs; and generating an alimentary element compatibility datum as a function of the physiological extraction of the plurality of physiological extractions using the trained alimentary element compatibility machine learning model.

Still referring to FIG. 10, in some embodiments, method 1000 may include identifying an inflammatory alimentary element as a function of the plurality of alimentary element compatibility data 1020. In some embodiments, the alimentary element compatibility machine learning model comprises a classifier trained to categorize inputs to categories representing severity of inflammatory response; and identifying the inflammatory alimentary element comprises selecting an inflammatory element within inflammatory element consumption data, where the inflammatory element consumption data describes consumption of the subject prior to a physiological extraction which alimentary element compatibility machine learning model categorizes as highly inflammatory. In some embodiments, each alimentary element consumption datum of the plurality of alimentary element consumption data is associated with an alimentary element compatibility datum of the plurality of alimentary element compatibility data; and identifying an inflammatory alimentary element comprises generating an alimentary element compatibility representation by categorizing alimentary element consumption data according to the associated alimentary element compatibility data.

Still referring to FIG. 10, in some embodiments, method 1000 may include pairing a medical professional with the subject as a function of the inflammatory alimentary element 1025. In some embodiments, pairing the medical professional with the subject comprises identifying a medial professional with experience providing guidance as to health effects of alimentary elements of a category including the inflammatory alimentary element.

Still referring to FIG. 10, in some embodiments, method 1000 may include displaying the inflammatory alimentary element using a user interface at a display device 1030.

Still referring to FIG. 10, in some embodiments, the method further comprises, using the at least a processor, transmitting to a remote device operated by the subject the alimentary element compatibility representation. In some embodiments, the method further comprises, using the at least a processor, receiving from the remote device operated by the subject an alimentary element annotation. In some embodiments, the method further comprises, using the at least a processor, receiving from the remote device operated by the subject an alimentary element selection. In some embodiments, the method further comprises using the at least a processor, receiving a subsequent physiological extraction of the subject, wherein the subsequent physiological extraction comprises an inflammation metric; using the at least a processor, receiving a subsequent alimentary element consumption datum describing consumption of the subject prior to the subsequent physiological extraction; using the at least a processor, generating a subsequent alimentary element compatibility datum for the subsequent alimentary element consumption datum by generating the subsequent alimentary element compatibility datum as a function of the subsequent physiological extraction using the trained alimentary element compatibility machine learning model; using the at least a processor, updating the alimentary element compatibility representation as a function of the subsequent alimentary element compatibility datum; and using the at least a processor, transmitting to the remote device operated by the subject the updated alimentary element compatibility representation.

Still referring to FIG. 10, some embodiments, the method further comprises, using the at least a processor, continuously receiving physiological extractions of a subject and identifying relevant physiological extractions as a function of alimentary element consumption timing.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
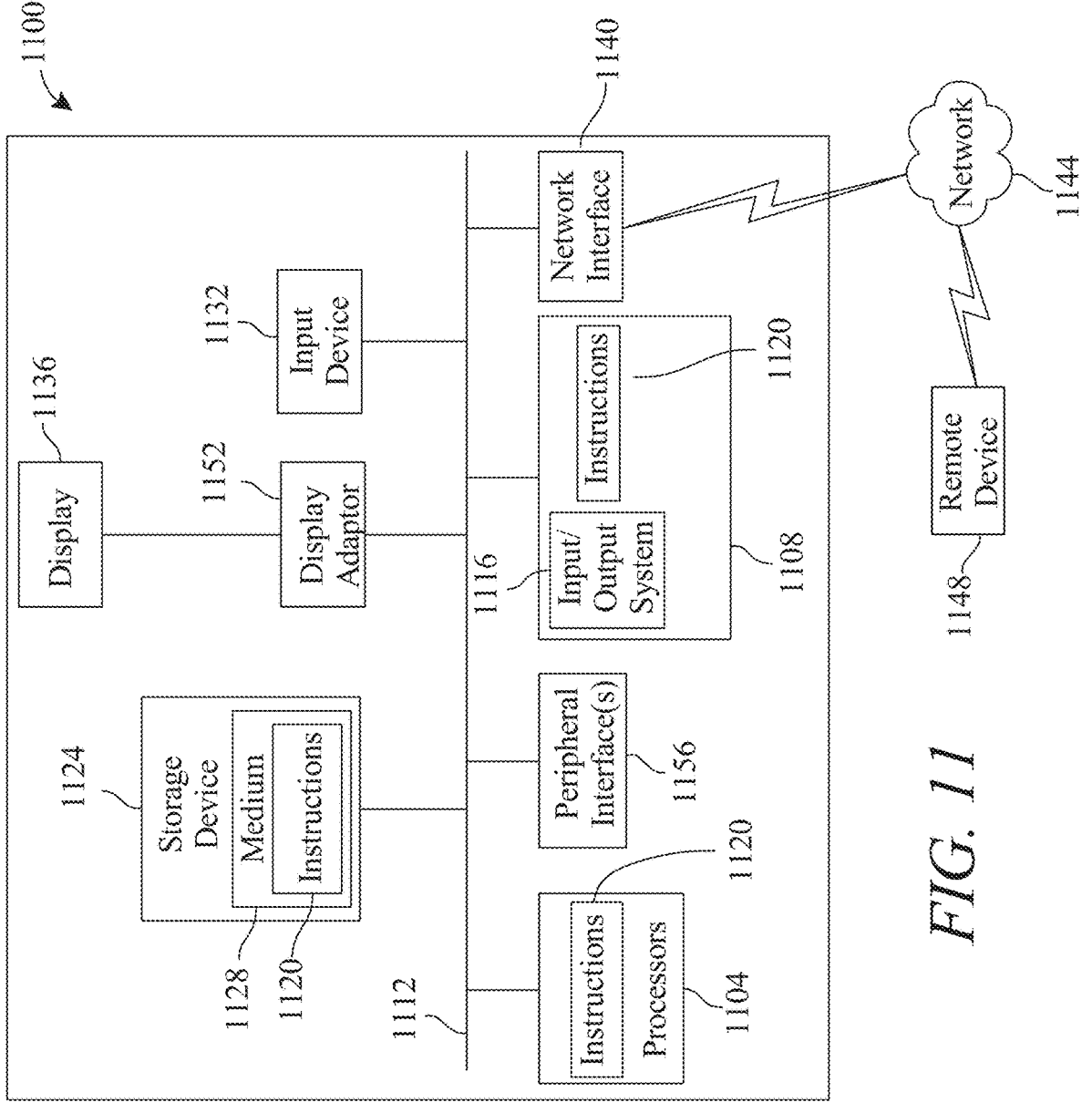
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIRE-WIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a food compatibility datum, wherein the system comprises a computing device configured to:

receive a plurality of physiological extractions of a subject, wherein the plurality of physiological extractions comprises at least an inflammation metric;

receive a plurality of alimentary element consumption data wherein each alimentary element consumption datum of the plurality of plurality of alimentary element consumption data describes a consumption of the subject prior to a physiological extraction of the plurality of physiological extractions;

generate a plurality of alimentary element compatibility data, wherein each alimentary element compatibility datum of the plurality of alimentary element compatibility data is associated with at least an alimentary element consumption datum of the plurality of alimentary element consumption data, wherein generating the plurality of alimentary element compatibility data comprises:

training an alimentary element compatibility machine learning model on a training dataset including a plurality of example physiological extractions and a plurality of example alimentary element consumption data as inputs correlated to a plurality of example alimentary element compatibility data as outputs; and generating an alimentary element compatibility datum as a function of the at least an inflammation metric and the plurality of alimentary element consumption data using the trained alimentary element compatibility machine learning model;

identify an inflammatory alimentary element as a function of the plurality of alimentary element compatibility data;

pair a medical professional with the subject as a function of the inflammatory alimentary element; and display the inflammatory alimentary element using a user interface at a display device.

2. The system of claim 1, wherein receiving the plurality of alimentary element consumption data comprises tracking the subject's historical consumptions of one or more alimentary elements with a set of predetermined alimentary elements.

3. The system of claim 1, wherein:

the alimentary element compatibility machine learning model comprises a classifier trained to classify the plurality of alimentary element consumption data into a plurality of categories representing different severity of an inflammatory response; and identifying the inflammatory alimentary element comprises selecting an instance of alimentary element consumption data within inflammatory element consumption data, where the inflammatory element consumption data describes consumption of the subject prior to a physiological extraction which alimentary element compatibility machine learning model categorizes as above a predetermined threshold of an inflammatory effect.

4. The system of claim 1, wherein identifying the inflammatory alimentary element comprises:

generating an alimentary element compatibility representation by categorizing the plurality of alimentary element consumption data according to the plurality of alimentary element compatibility data.

5. The system of claim 4, wherein the computing device is configured to transmit to a remote device operated by the subject the alimentary element compatibility representation.

6. The system of claim 5, wherein the computing device is configured to receive from the remote device operated by the subject an alimentary element annotation.

7. The system of claim 5, wherein the computing device is configured to receive from the remote device operated by the subject an alimentary element selection.

8. The system of claim 5, wherein the computing device is configured to:

update the alimentary element compatibility representation as a function of a subsequent alimentary element compatibility datum; and transmit to the remote device operated by the subject the updated alimentary element compatibility representation.

9. The system of claim 1, wherein the computing device is configured to:

continuously receive physiological extractions of a subject; and identify a subset of the continuously received physiological extractions as a function of alimentary element consumption timing.

10. The system of claim 1, wherein pairing the medical professional with the subject comprises:

identifying the medial professional with experience providing guidance as to health effects of alimentary elements of a category including the inflammatory alimentary element.

11. A method of generating a food compatibility datum, wherein the method comprises:

using at least a processor, receiving a plurality of physiological extractions of a subject, wherein the plurality of physiological extractions comprises at least an inflammation metric;

using the at least a processor, receiving a plurality of alimentary element consumption data wherein each alimentary element consumption datum of the plurality of plurality of alimentary element consumption data describes a consumption of the subject prior to a physiological extraction of the plurality of physiological extractions;

using the at least a processor, generating a plurality of alimentary element compatibility data, wherein each alimentary element compatibility datum of the plurality of alimentary element compatibility data is associated with at least an alimentary element consumption datum of the plurality of alimentary element consumption data, wherein generating the plurality of alimentary element compatibility data comprises:

training an alimentary element compatibility machine learning model on a training dataset including a plurality of example physiological extractions and a plurality of example alimentary element consumption data as inputs correlated to a plurality of example alimentary element compatibility data as outputs; and generating an alimentary element compatibility datum as a function of the at least an inflammation metric and the plurality of alimentary element consumption data using the trained alimentary element compatibility machine learning model;

using the at least a processor, identifying an inflammatory alimentary element as a function of the plurality of alimentary element compatibility data;

using the at least a processor, pairing a medical professional with the subject as a function of the inflammatory alimentary element; and using the at least a processor, displaying the inflammatory alimentary element using a user interface at a display device.

12. The method of claim 11, wherein receiving the plurality of alimentary element consumption data comprises tracking the subject's historical consumptions of one or more alimentary elements with a set of predetermined alimentary elements.

13. The method of claim 11, wherein:

the alimentary element compatibility machine learning model comprises a classifier trained to classify the plurality of alimentary element consumption data into a plurality of categories representing different severity of an inflammatory response; and identifying the inflammatory alimentary element comprises selecting an instance of alimentary element consumption data within inflammatory element consumption data, where the inflammatory element consumption data describes consumption of the subject prior to a physiological extraction which alimentary element compatibility machine learning model categorizes as above a predetermined threshold of an inflammatory effect.

14. The method of claim 11, wherein identifying the inflammatory alimentary element comprises:

generating an alimentary element compatibility representation by categorizing the plurality of alimentary element consumption data according to the plurality of alimentary element compatibility data.

15. The method of claim 14, further comprises:

using the at least a processor, transmitting to a remote device operated by the subject the alimentary element compatibility representation.

16. The method of claim 15, further comprises:

using the at least a processor, receiving from the remote device operated by the subject an alimentary element annotation.

17. The method of claim 15, further comprises:

using the at least a processor, receiving from the remote device operated by the subject an alimentary element selection.

18. The method of claim 15, further comprises:

using the at least a processor, updating the alimentary element compatibility representation as a function of a subsequent alimentary element compatibility datum; and using the at least a processor, transmitting to the remote device operated by the subject the updated alimentary element compatibility representation.

19. The method of claim 11, further comprises:

using the at least a processor, continuously receiving physiological extractions of a subject; and using the at least a processor, identifying a subset of the continuously received physiological extractions as a function of alimentary element consumption timing.

20. The method of claim 11, wherein pairing the medical professional with the subject comprises:

identifying the medial professional with experience providing guidance as to health effects of alimentary elements of a category including the inflammatory alimentary element.

* * * * *